United States Patent
Petruno et al.

(10) Patent No.: US 9,989,527 B2
(45) Date of Patent: *Jun. 5, 2018

(54) LATERAL FLOW ASSAY SYSTEMS AND METHODS

(71) Applicant: Alverix, Inc., San Jose, CA (US)

(72) Inventors: Patrick T. Petruno, San Jose, CA (US); John F. Petrilla, San Jose, CA (US); Michael J. Brosnan, San Jose, CA (US); Rong Zhou, San Jose, CA (US); Daniel B. Roitman, San Jose, CA (US)

(73) Assignee: Alverix, Inc., Franklin Lakes, NJ (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/005,776

(22) Filed: Jan. 25, 2016

(65) Prior Publication Data
US 2016/0313254 A1 Oct. 27, 2016

Related U.S. Application Data

(60) Continuation of application No. 14/019,166, filed on Sep. 5, 2013, now Pat. No. 9,243,997, which is a
(Continued)

(51) Int. Cl.
*G01N 33/543* (2006.01)
*G01N 21/84* (2006.01)
(Continued)

(52) U.S. Cl.
CPC ....... *G01N 33/54386* (2013.01); *G01N 21/17* (2013.01); *G01N 21/274* (2013.01);
(Continued)

(58) Field of Classification Search
CPC ............. G01N 21/8483; G01N 33/558; G01N 2021/6439; G01N 21/17; G01N 21/6428;
(Continued)

(56) References Cited

U.S. PATENT DOCUMENTS 4,849,338 A 7/1989 Litman et al.
4,902,278 A 2/1990 Maget et al.
(Continued)

FOREIGN PATENT DOCUMENTS

CA 2210559 1/1998
JP H09297832 A 11/1997
(Continued)

*Primary Examiner* — Samuel P Siefke
(74) *Attorney, Agent, or Firm* — Knobbe Martens Olson & Bear LLP

(57) ABSTRACT

In one aspect, a diagnostic test system includes a housing, a reader, and a data analyzer. The housing includes a port for receiving a test strip. The reader obtains separable light intensity measurements from localized regions of an area of the detection zone exposed for optical inspection, wherein each of the localized regions is characterized by at least one surface dimension smaller than the first dimension. The data analyzer identifies ones of the light intensity measurements obtained from the at least one test region and computes at least one parameter from the identified ones of the light intensity measurements. In another aspect, the reader obtains a respective set of light intensity measurements from each of multiple corresponding regions of the exposed surface area of the detection zone, and the data analyzer computes at least one parameter from at least one of the sets of light intensity measurements.

18 Claims, 7 Drawing Sheets

Related U.S. Application Data continuation of application No. 13/360,081, filed on Jan. 27, 2012, now Pat. No. 9,091,631, which is a division of application No. 11/112,807, filed on Apr. 22, 2005, now Pat. No. 8,128,871, which is a continuation-in-part of application No. 11/044,394, filed on Jan. 26, 2005, which is a division of application No. 10/816,636, filed on Apr. 1, 2004.

(51) Int. Cl.
| | |
|---|---|
| *G01N 33/558* | (2006.01) |
| *G01N 21/17* | (2006.01) |
| *G01N 21/64* | (2006.01) |
| *G01N 21/27* | (2006.01) |

(52) U.S. Cl.
CPC ..... *G01N 21/6428* (2013.01); *G01N 21/8483* (2013.01); *G01N 33/558* (2013.01); *G01N 2021/6439* (2013.01); *G01N 2201/062* (2013.01); *G01N 2201/067* (2013.01); *Y10S 435/805* (2013.01); *Y10S 435/823* (2013.01); *Y10S 436/807* (2013.01); *Y10S 436/809* (2013.01); *Y10S 436/81* (2013.01); *Y10S 436/823* (2013.01); *Y10T 436/25125* (2015.01)

(58) Field of Classification Search
CPC ....... G01N 2201/062; G01N 2201/067; G01N 33/54386; G01N 2021/6441
See application file for complete search history.

(56) References Cited

U.S. PATENT DOCUMENTS

| | | | |
|---|---|---|---|
| 4,916,056 | A | 4/1990 | Brown et al. |
| 4,960,691 | A | 10/1990 | Gordon et al. |
| 5,030,558 | A | 7/1991 | Litman et al. |
| 5,132,097 | A | 7/1992 | Van Deusen et al. |
| 5,217,832 | A | 6/1993 | Joslin et al. |
| 5,281,395 | A | 1/1994 | Markart et al. |
| 5,304,813 | A | 4/1994 | De Man |
| 5,371,687 | A | 12/1994 | Holmes, II et al. |
| 5,424,220 | A | 6/1995 | Goerlach-Graw et al. |
| 5,442,169 | A | 8/1995 | Kunz |
| 5,514,602 | A | 5/1996 | Brooks et al. |
| 5,519,210 | A | 5/1996 | Berner |
| 5,550,362 | A | 8/1996 | Sherman |
| 5,559,041 | A | 9/1996 | Kang et al. |
| 5,580,794 | A | 12/1996 | Allen |
| 5,602,040 | A | 2/1997 | May et al. |
| 5,837,546 | A | 11/1998 | Allen et al. |
| 5,856,203 | A | 1/1999 | Robinson et al. |
| 5,861,256 | A | 1/1999 | Glass et al. |
| 5,961,451 | A | 10/1999 | Reber et al. |
| 6,017,767 | A | 1/2000 | Chandler |
| 6,136,610 | A | 10/2000 | Polito et al. |
| 6,180,409 | B1 | 1/2001 | Howard et al. |
| 6,217,744 | B1 | 4/2001 | Crosby |
| 6,235,241 | B1 | 5/2001 | Catt et al. |
| 6,267,722 | B1 | 7/2001 | Anderson et al. |
| 6,268,162 | B1 | 7/2001 | Phillips et al. |
| 6,274,323 | B1 | 8/2001 | Bruchez et al. |
| 6,281,785 | B1 | 8/2001 | Hamaguchi |
| 6,300,141 | B1 | 10/2001 | Segal et al. |
| 6,326,144 | B1 | 12/2001 | Bawendi et al. |
| 6,377,894 | B1 | 4/2002 | Deweese et al. |
| 6,379,622 | B1 | 4/2002 | Polak et al. |
| 6,394,952 | B1 | 5/2002 | Anderson et al. |
| 6,403,037 | B1 | 6/2002 | Chang et al. |
| 6,483,582 | B2 | 11/2002 | Modlin et al. |
| 6,561,643 | B1 | 5/2003 | Walker et al. |
| 6,585,341 | B1 | 7/2003 | Walker et al. |
| 6,607,922 | B2 | 8/2003 | LaBorde |
| 6,611,634 | B2 | 8/2003 | Herron et al. |
| 6,629,057 | B2 | 9/2003 | Zweig et al. |
| 6,630,307 | B2 | 10/2003 | Bruchez et al. |
| 6,656,744 | B2 | 12/2003 | Pronovost et al. |
| 6,663,833 | B1 | 12/2003 | Stave et al. |
| 6,671,428 | B1 | 12/2003 | Yang et al. |
| 6,673,622 | B1 | 1/2004 | Jina |
| 6,673,630 | B2 | 1/2004 | Albarella et al. |
| 6,686,170 | B1 | 2/2004 | Flanders et al. |
| 6,713,271 | B1 | 3/2004 | Feistel et al. |
| 6,732,917 | B1 | 5/2004 | Benz et al. |
| 6,750,963 | B2 | 6/2004 | Sampas |
| 6,855,561 | B2 | 2/2005 | Jerome et al. |
| 6,875,185 | B2 | 4/2005 | Wong et al. |
| 6,966,880 | B2 | 11/2005 | Boecker et al. |
| 7,378,285 | B2 | 5/2008 | Lambotte et al. |
| 7,521,260 | B2 | 4/2009 | Petruno et al. |
| 7,678,566 | B2 | 3/2010 | Miyoshi et al. |
| 8,043,867 | B2 | 10/2011 | Petruno et al. |
| 8,128,871 | B2 | 3/2012 | Petruno et al. |
| 9,243,997 | B2 | 1/2016 | Petruno et al. |
| 2001/0034068 | A1 | 10/2001 | Spivey et al. |
| 2001/0035990 | A1 | 11/2001 | Mok et al. |
| 2002/0004246 | A1 | 1/2002 | Daniels et al. |
| 2002/0146844 | A1 | 10/2002 | Pronovost et al. |
| 2002/0169439 | A1 | 11/2002 | Flaherty |
| 2002/0176927 | A1 | 11/2002 | Kodas et al. |
| 2003/0003601 | A1 | 1/2003 | Some et al. |
| 2003/0082516 | A1 | 5/2003 | Straus |
| 2003/0119202 | A1 | 6/2003 | Kaylor et al. |
| 2003/0119203 | A1 | 6/2003 | Wei et al. |
| 2003/0143580 | A1 | 7/2003 | Straus |
| 2003/0171697 | A1 | 9/2003 | Smith et al. |
| 2003/0174743 | A1 | 9/2003 | Cliché et al. |
| 2003/0175820 | A1 | 9/2003 | Smith et al. |
| 2003/0201176 | A1 | 10/2003 | Mills et al. |
| 2003/0207454 | A1 | 11/2003 | Eyster et al. |
| 2003/0222198 | A1 | 12/2003 | Olszak et al. |
| 2004/0012783 | A1 | 1/2004 | Morokawa et al. |
| 2004/0014202 | A1 | 1/2004 | King et al. |
| 2004/0018637 | A1 | 1/2004 | Polito et al. |
| 2004/0043502 | A1 | 3/2004 | Song et al. |
| 2004/0063219 | A1 | 4/2004 | Bateman et al. |
| 2004/0096169 | A1 | 5/2004 | Sone et al. |
| 2004/0151632 | A1 | 8/2004 | Badley et al. |
| 2004/0152209 | A1 | 8/2004 | Zin et al. |
| 2004/0214347 | A1 | 10/2004 | LaBorde et al. |
| 2005/0033196 | A1 | 2/2005 | Alroy |
| 2005/0037510 | A1 | 2/2005 | Sharrock et al. |
| 2005/0130164 | A1 | 6/2005 | Akimoto et al. |
| 2005/0221504 | A1 | 10/2005 | Petruno et al. |
| 2005/0221505 | A1 | 10/2005 | Petruno et al. |
| 2006/0014302 | A1 | 1/2006 | Martinez et al. |
| 2006/0121625 | A1 | 6/2006 | Clemens et al. |
| 2006/0122782 | A1 | 6/2006 | Petrilla et al. |
| 2006/0126063 | A1 | 6/2006 | Cluzel et al. |
| 2006/0210435 | A1 | 9/2006 | Alvavie et al. |
| 2006/0216696 | A1 | 9/2006 | Goguen |
| 2006/0240541 | A1 | 10/2006 | Petruno et al. |
| 2006/0240568 | A1 | 10/2006 | Petruno et al. |
| 2007/0081920 | A1 | 4/2007 | Murphy et al. |
| 2007/0185679 | A1 | 8/2007 | Petruno et al. |
| 2007/0231922 | A1 | 10/2007 | Petruno et al. |
| 2009/0180925 | A1 | 7/2009 | Petruno et al. |
| 2009/0180926 | A1 | 7/2009 | Petruno et al. |
| 2009/0180927 | A1 | 7/2009 | Petruno et al. |
| 2009/0180928 | A1 | 7/2009 | Petruno et al. |
| 2009/0180929 | A1 | 7/2009 | Petruno et al. |
| 2009/0214383 | A1 | 8/2009 | Petruno et al. |
| 2012/0129272 | A1 | 5/2012 | Petruno et al. |
| 2014/0004624 | A1 | 1/2014 | Petruno et al. |
| 2017/0199183 | A1 | 7/2017 | Petruno et al. |

FOREIGN PATENT DOCUMENTS

| | | |
|---|---|---|
| JP | H11108927 A | 4/1999 |
| JP | 2001033454 A | 2/2001 |
| JP | 2001066277 A | 3/2001 |
| WO | WO 1988/008534 | 11/1988 |
| WO | WO 1995/013531 | 5/1995 |

(56) References Cited

FOREIGN PATENT DOCUMENTS

| | | |
|---|---|---|
| WO | WO 1999/041596 | 8/1999 |
| WO | WO 2000/031538 | 6/2000 |
| WO | WO 2001/057502 | 8/2001 |
| WO | WO 2003/065009 | 8/2003 |
| WO | WO 2003/098278 | 11/2003 |
| WO | WO 2004/003527 | 1/2004 |

LATERAL FLOW ASSAY SYSTEMS AND METHODS

CROSS-REFERENCE TO RELATED APPLICATIONS

This application is a continuation of U.S. application Ser. No. 14/019,166, filed Sep. 5, 2013 and scheduled to issue on Jan. 26, 2016 as U.S. Pat. No. 9,243,997, which is a continuation of U.S. application Ser. No. 13/360,081, filed Jan. 27, 2012 and issued as U.S. Pat. No. 9,091,631 on Jul. 28, 2015, which is a divisional of U.S. application Ser. No. 11/112,807, filed Apr. 22, 2005 and issued as U.S. Pat. No. 8,128,871 on Mar. 6, 2012, which is a continuation-in-part of U.S. application Ser. No. 11/044,394, filed Jan. 26, 2005, which is a divisional of U.S. application Ser. No. 10/816,636, filed Apr. 1, 2004, all of which are incorporated by reference in their entirety.

BACKGROUND

Lateral flow assay test kits are currently available for testing for a wide variety of medical and environmental conditions or compounds, such as a hormone, a metabolite, a toxin, or a pathogen-derived antigen. FIG. 1 shows a typical lateral flow test strip 10 that includes a sample receiving zone 12, a labeling zone 14, a detection zone 15, and an absorbent zone 20 on a common substrate 22. These zones 12-20 typically are made of a material (e.g., chemically-treated nitrocellulose) that allows fluid to flow from the sample receiving zone 12 to the absorbent zone 220 by capillary action. The detection zone 15 includes a test region 16 for detecting the presence of a target analyte in a fluid sample and a control region 18 for indicating the completion of an assay test.

FIGS. 2A and 2B show an assay performed by an exemplary implementation of the test strip 10. A fluid sample 24 (e.g., blood, urine, or saliva) is applied to the sample receiving zone 12. In the example shown in FIGS. 2A and 2B, the fluid sample 24 includes a target analyte 26 (i.e., a molecule or compound that can be assayed by the test strip 10). Capillary action draws the liquid sample 24 downstream into the labeling zone 14, which contains a substance 28 for indirect labeling of the target analyte 16. In the illustrated example, the labeling substance 28 consists of an immunoglobulin 30 with an attached dye molecule 32. The immunoglobulin 30 specifically binds the target analyte 26 to form a labeled target analyte complex. In some other implementations, the labeling substance 28 is a non-immunoglobulin labeled compound that specifically binds the target analyte 26 to form a labeled target analyte complex.

The labeled target analyte complexes, along with excess quantities of the labeling substance, are carried along the lateral flow path into the test region 16, which contains immobilized compounds 34 that are capable of specifically binding the target analyte 26. In the illustrated example, the immobilized compounds 34 are immunoglobulins that specifically bind the labeled target analyte complexes and thereby retain the labeled target analyte complexes in the test region 16. The presence of the labeled analyte in the sample typically is evidenced by a visually detectable coloring of the test region 16 that appears as a result of the accumulation of the labeling substance in the test region 16.

The control region 18 typically is designed to indicate that an assay has been performed to completion. Compounds 35 in the control region 18 bind and retain the labeling substance 28. The labeling substance 28 typically becomes visible in the control region 18 after a sufficient quantity of the labeling substance 28 has accumulated. When the target analyte 26 is not present in the sample, the test region 16 will not be colored, whereas the control region 18 will be colored to indicate that assay has been performed. The absorbent zone 20 captures excess quantities of the fluid sample 24.

Although visual inspection of lateral flow assay devices of the type described above are able to provide qualitative assay results, such a method of reading these types of devices is unable to provide quantitative assay measurements and therefore is prone to misinterpretation errors. Automated and semi-automated lateral flow assay readers have been developed in an effort to overcome this deficiency.

In one approach, a portable lateral flow assay reader performs assays on bodily fluids to detect the presence of certain hormones, glucose, or other bodily fluids of interest. Membrane test strips containing a fluid sample are inserted directly into a receiving port of a reader. The receiving port is shielded to improve sensitivity and reduce the entry of stray or ambient light into the reader. The reader includes a light source and one or more sensors that detect the intensity of light reflected from the detection zones of the test strips that are inserted into the receiving port.

In another approach, a reader detects an intensity of a detection signal arising in one or more measurement zones in a detection zone of a lateral flow assay test strip as a result of the presence of an immobilized labeled target analyte complex. The reader generates a baseline of signal intensity from the measurement zones by interpolating between values of the detection signal outside of the measurement zones and inside of the detection zone. The reader quantifies a value of signal intensity representative of the immobilized labeled target analyte complex with respect to the baseline. In this process, the reader locates a beginning boundary and an ending boundary for the one or more measurement zones on the test strip, allowing an automatic or semi-automatic analytical instrument, or a human reader, to determine certain results of the lateral flow assay. The signals from the measurement zones are quantified or compared with respect to the baseline. Quantified values corresponding to the respective concentration of compounds in different measurement zones may then be compared with one another to detect the presence of antigens in the sample.

The measurements that are made by the above-described lateral flow assay readers are based on signals from regions of the test strips that typically are significantly larger than the regions of interest. As a result, these measurements tend to have high noise levels and, consequently, these measurements may yield inaccurate or incorrect results when low concentrations of analytes are involved.

SUMMARY

In one aspect, the invention features a diagnostic test system that includes a housing, a reader, and a data analyzer. The housing includes a port for receiving a test strip. The test strip supports lateral flow of a fluid sample along a lateral flow direction and includes a labeling zone containing a labeling substance that binds a label to a target analyte and a detection zone comprising at least one test region containing an immobilized substance that binds the target analyte. The detection zone includes an area that is exposed for optical inspection and is characterized by a first dimension transverse to the lateral flow direction and a second dimension parallel to the lateral flow direction. The reader is configured to obtain separable light intensity measurements from localized regions of the exposed area of the detection zone when the test strip is loaded in the port, wherein each of the localized regions is characterized by at least one surface dimension smaller than the first dimension. The data analyzer is operable to identify ones of the light intensity measurements obtained from the at least one test region and to compute at least one parameter from the identified ones of the light intensity measurements.

In another aspect, the invention features a diagnostic test system that includes a housing, a reader, and a data analyzer. The housing includes a port for receiving a test strip. The test strip supports lateral flow of a fluid sample along a lateral flow direction and includes a labeling zone containing a labeling substance that binds a label to a target analyte and a detection zone comprising at least one test region containing an immobilized substance that binds the target analyte and an area that is exposed for optical inspection. The reader is configured to obtain a respective set of light intensity measurements from each of multiple corresponding regions of the exposed surface area of the detection zone when the test strip is loaded in the port. The data analyzer is operable to compute at least one parameter from at least one of the sets of light intensity measurements.

In another aspect, the invention features a diagnostic test method. In accordance with this inventive method, a test strip is received. The test strip supports lateral flow of a fluid sample along a lateral flow direction and includes a labeling zone containing a labeling substance that binds a label to a target analyte and a detection zone comprising at least one test region containing an immobilized substance that binds the target analyte. The detection zone includes an area that is exposed for optical inspection and is characterized by a first dimension transverse to the lateral flow direction and a second dimension parallel to the lateral flow direction. Separable light intensity measurements are obtained from localized regions of the exposed area of the detection zone, wherein each of the localized regions is characterized by at least one surface dimension smaller than the first dimension. Ones of the light intensity measurements obtained from the at least one test region are identified. At least one parameter is computed from the identified ones of the light intensity measurements.

In another aspect, the invention features a diagnostic test method. In accordance with this inventive method, a test strip is received. The test strip supports lateral flow of a fluid sample along a lateral flow direction and includes a labeling zone containing a labeling substance that binds a label to a target analyte and a detection zone comprising at least one test region containing an immobilized substance that binds the target analyte and an area that is exposed for optical inspection. A respective set of light intensity measurements is obtained from each of multiple corresponding regions of the exposed surface area of the detection zone when the test strip is loaded in the port. At least one parameter is computed from at least one of the sets of light intensity measurements.

Other features and advantages of the invention will become apparent from the following description, including the drawings and the claims.

DETAILED DESCRIPTION

In the following description, like reference numbers are used to identify like elements. Furthermore, the drawings are intended to illustrate major features of exemplary embodiments in a diagrammatic manner. The drawings are not intended to depict every feature of actual embodiments nor relative dimensions of the depicted elements, and are not drawn to scale.

Some of the embodiments that are described in detail below reduce levels of noise (e.g., noise caused by reflection of light or intrinsic fluorescence from materials in the test strip) in lateral flow assay measurements by restricting the measurements to the regions of interest on the test strip from which the desired quantitative information may be derived.

In this way, these embodiments increase the signal-to-noise levels of these measurements and, thereby, increase measurement sensitivity and reduce the incidence of erroneous results for low concentrations of analytes. Some of these embodiments also increase the accuracy of the lateral flow assay results by obtaining respective sets of measurements from localized regions of the test strip from which additional analytical information about these regions may be obtained. This additional information may be used to isolate target measurements from background noise and to derive more accurate estimates of target parameter values. Some embodiments also are capable of accurately reading multiple analytes from the same test strip.

I. Diagnostic Test System Overview

Figure 3:
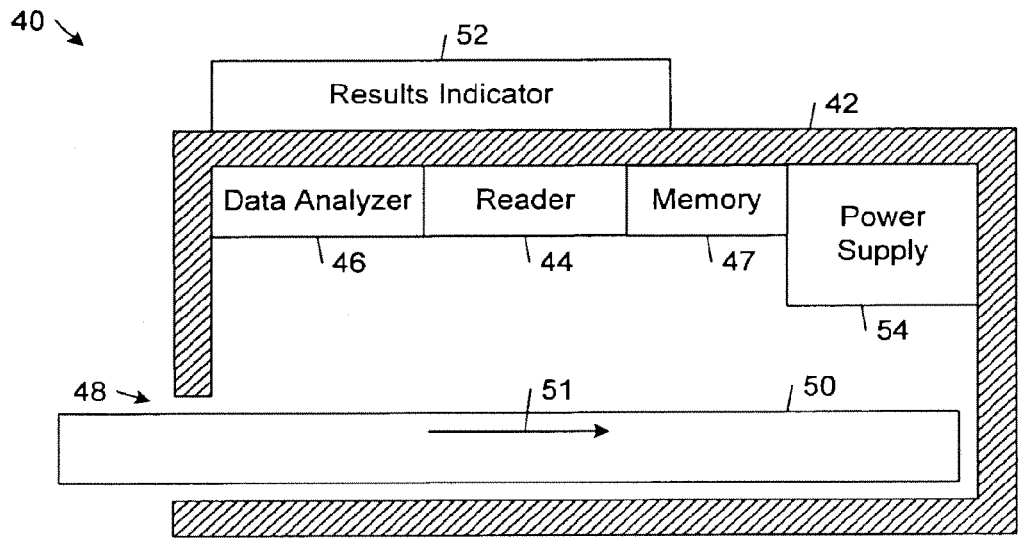
FIG. 3 is a block diagram of a test strip that is loaded into an embodiment of a diagnostic test system.

FIG. 3 shows an embodiment of a diagnostic test system 40 that includes a housing 42, a reader 44, a data analyzer 46, and a memory 47. The housing 42 includes a port 48 for receiving a test strip 50. When the test strip 50 is loaded in the port 48, the reader 44 obtains light intensity measurements from the test strip 50. In general, the light intensity measurements may be unfiltered or they may be filtered in terms of at least one of wavelength and polarization. The data analyzer 46 computes at least one parameter from one or more of the light intensity measurements. A results indicator 52 provides an indication of one or more of the results of an assay of the test strip 50. In some implementations, the diagnostic test system 40 is fabricated from relatively inexpensive components enabling it to be used for disposable or single-use applications.

The housing 42 may be made of any one of a wide variety of materials, including plastic and metal. The housing 42 forms a protective enclosure for the reader 44, the data analyzer 46, the power supply 54, and other components of the diagnostic test system 40. The housing 42 also defines a receptacle that mechanically registers the test strip 50 with respect to the reader 44. The receptacle may be designed to receive any one of a wide variety of different types of test strips 50, including test strips of the type shown in FIG. 1.

In general, each of the test strips 50 supports lateral flow of a fluid sample along a lateral flow direction 51 and includes a labeling zone containing a labeling substance that binds a label to a target analyte and a detection zone that includes at least one test region containing an immobilized substance that binds the target analyte. One or more areas of the detection zone, including at least a portion of the test region, are exposed for optical inspection by the reader 44. The exposed areas of the detection zone may or may not be covered by an optically transparent window.

The reader 44 includes one or more optoelectronic components for optically inspecting the exposed areas of the detection zone of the test strip 50. In some implementations, the reader 44 includes at least one light source and at least one light detector. In some implementations, the light source may include a semiconductor light-emitting diode and the light detector may include a semiconductor photodiode. Depending on the nature of the label that is used by the test strip 50, the light source may be designed to emit light within a particular wavelength range or light with a particular polarization. For example, if the label is a fluorescent label, such as a quantum dot, the light source would be designed to illuminate the exposed areas of the detection zone of the test strip 50 with light in a wavelength range that induces fluorescence from the label. Similarly, the light detector may be designed to selectively capture light from the exposed areas of the detection zone. For example, if the label is a fluorescent label, the light detector would be designed to selectively capture light within the wavelength range of the fluorescent light emitted by the label or with light of a particular polarization. On the other hand, if the label is a reflective-type label, the light detector would be designed to selectively capture light within the wavelength range of the light emitted by the light source. To these ends, the light detector may include one or more optical filters that define the wavelength ranges or polarizations axes of the captured light.

The data analyzer 46 processes the light intensity measurements that are obtained by the reader 44. In general, the data analyzer 46 may be implemented in any computing or processing environment, including in digital electronic circuitry or in computer hardware, firmware, or software. In some embodiments, the data analyzer 46 includes a processor (e.g., a microcontroller, a microprocessor, or ASIC) and an analog-to-digital converter. In the illustrated embodiment, the data analyzer 46 is incorporated within the housing 42 of the diagnostic test system 40. In other embodiments, the data analyzer 46 is located in a separate device, such as a computer, that may communicate with the diagnostic test system 40 over a wired or wireless connection.

In general, the results indicator 52 may include any one of a wide variety of different mechanisms for indicating one or more results of an assay test. In some implementations, the results indicator 52 includes one or more lights (e.g., light-emitting diodes) that are activated to indicate, for example, a positive test result and the completion of the assay test (i.e., when sufficient quantity of labeling substance 28 has accumulated in the control region). In other implementations, the results indicator 52 includes an alphanumeric display (e.g., a two or three character light-emitting diode array) for presenting assay test results.

A power supply 54 supplies power to the active components of the diagnostic test system 40, including the reader 44, the data analyzer 46, and the results indicator 52. The power supply 54 may be implemented by, for example, a replaceable battery or a rechargeable battery.

II. Diagnostic Testing Based on Separable Localized Light Intensity Measurements The embodiments that are described in detail below reduce levels of noise (e.g., noise caused by intrinsic fluorescence from materials in the test strip) in lateral flow assay measurements by restricting the measurements to the regions of interest on the test strip from which desired quantitative information may be derived. In this way, these embodiments increase the signal-to-noise levels of these measurements and, thereby, improve measurement sensitivity and reduce the incidence of erroneous results.

Figure 4:
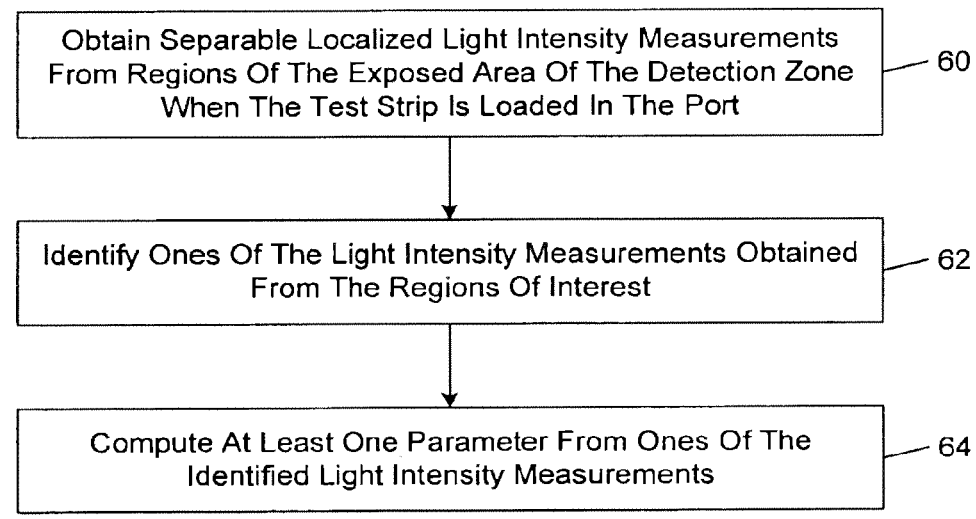
FIG. 4 is a flow diagram of an embodiment of a diagnostic test method.

FIG. 4 shows an embodiment of a diagnostic test method that is executable by the implementations of the diagnostic test system 40 described below. In accordance with this method, the reader 44 obtains separable localized light intensity measurements from regions of the exposed area of the detection zone of the test strip 50 when the test strip 50 is loaded in the port 48 of the diagnostic test system 40 (block 60). As used herein, the term "separable localized light intensity measurements" refers to the ability of the reader to 44 to transmit or record the light intensity measurements from respective localized regions of the test strip in a way that allows the data analyzer 46 to individually analyze each of the light intensity measurements.

In this embodiment, each of the separable localized regions from which the light intensity measurements are obtained by the reader 44 is characterized by at least one surface dimension that is smaller than the dimension of the exposed area of the detection zone that is transverse to the lateral flow direction. In some implementations, each of these localized regions has a surface dimension that is approximately the same size or smaller than the narrowest dimension of a region of interest in the detection zone (e.g., the test region, the control region, or a region of an immobilized labeled or unlabeled complex).

After the reader 44 has obtained light intensity measurements from such localized regions of interest in the detection zone (block 60), the data analyzer 46 identifies ones of the light intensity measurements obtained from the regions of interest (block 62). In this process, the data analyzer 46 isolates the measurements corresponding to regions of interest from the measurements corresponding to other regions of the test strip 50. The isolated measurements have higher signal-to-noise ratios than aggregated measurements that include measurements from regions outside of the regions of interest.

The data analyzer 46 can then compute at least one parameter from ones of the identified light intensity measurements (block 64). Exemplary parameters include peak intensity and aggregate intensity values. Since the measurements that are used to compute these parameters have higher signal-to-noise ratios, they characterize the region of interest with greater accuracy and, thereby, improve the results of the lateral flow assay.

Figure 1:
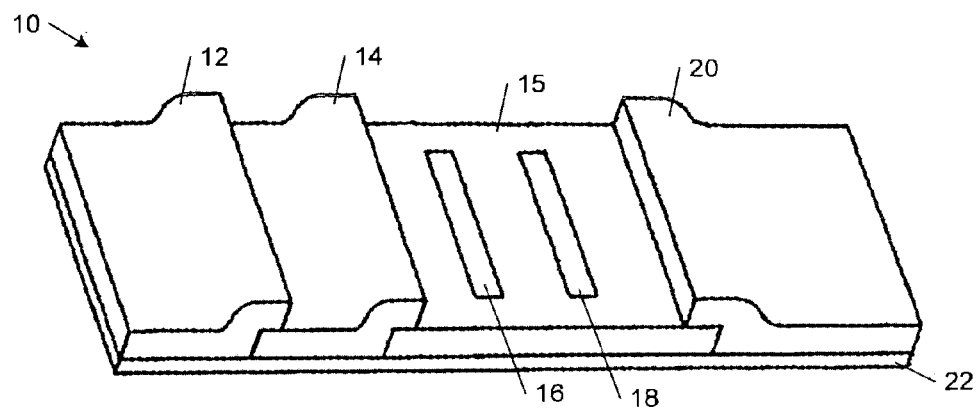
FIG. 1 is a diagrammatic view of a prior art implementation of a lateral flow assay test strip.
Figure 2A:
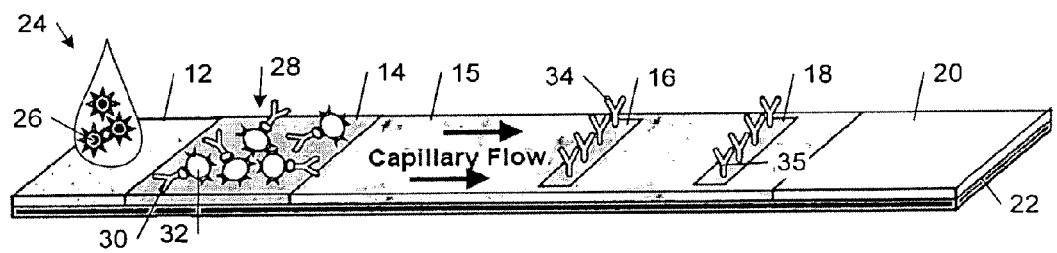
FIG. 2A is a diagrammatic view of a fluid sample being applied to an application zone of the lateral flow assay test strip shown in FIG. 1.
Figure 2B:
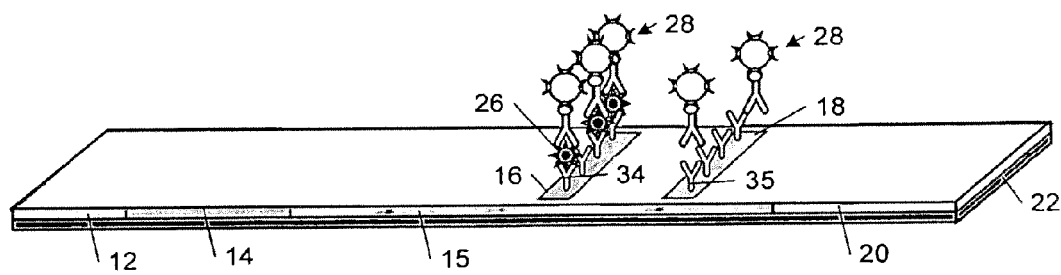
FIG. 2B is a diagrammatic view of the lateral flow assay test strip shown in FIG. 2A after the fluid sample has flowed across the test strip to an absorption zone.
Figure 5A:
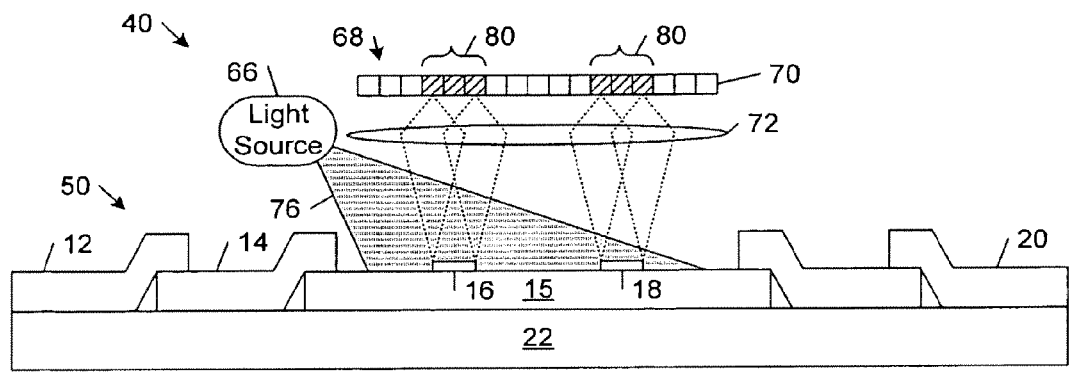
FIG. 5A is a diagrammatic side view of an implementation of the diagnostic test system shown in FIG. 3 that includes a two-dimensional light detector array obtaining light intensity measurements from regions of a test strip.

A. Obtaining Separable Localized Light Intensity Measurements Using a Two-Dimensional Light Detector Array FIG. 5A shows an implementation of the diagnostic test system 40 that includes a light source 66, a two-dimensional array 68 of light detectors 70, and a lens 72. In FIG. 5A, the test strip 50 is substantially the same as the test strip 10, which is shown in FIG. 1. In particular, the test strip 50 includes the sample receiving zone 12, the labeling zone 14, the detection zone 15, and the absorbent zone 20 on the common substrate 22. In the illustrated implementation, a substantial portion of the detection zone 15 is exposed for optical inspection.

In operation, the light source 66 illuminates with light 76 the exposed portion of the detection zone 15, including the test region 16 and the control region 18 of the test strip 50. The illuminating light may be broadband or narrowband and may be polarized or non-polarized. The light detector array 68 obtains separable localized light intensity measurements from the illuminated regions of the detection zone 15. In general, the light intensity measurements may be unfiltered or they may be filtered in terms of at least one of wavelength and polarization. The light detector array 68 may be synchronized with the light source 66. In general, the light detector array 68 may measure light intensity while the detection zone 15 is being illuminated or after the light source 66 has illuminated the detection zone 15. Light reflected or fluorescing from the detection zone 15 is focused by the lens 72 onto the individual light detectors 70 of the light detector array 68. Each of the light detectors 70 receives light from a respective localized region of the detection zone 15. That is, each light detector 70 is able to resolve or separably image a respective localized region of the detection zone 15. In this implementation, the localized regions are characterized by a surface dimension that is at most as large as the narrowest dimension of the test and control regions 16, 18 (i.e., the dimensions of regions 16, 18 that are along the lateral flow direction). In the illustrated implementations, the localized regions are characterized by square dimensions that are approximately equal to one-third of the size of the test and control regions 16, 18 along the lateral flow direction. The light detectors 70 produce signals representative of the amount of light received from the respective localized regions. These signals may be stored in a memory or they may be transmitted to the data analyzer 46 for processing.

Figure 5B:
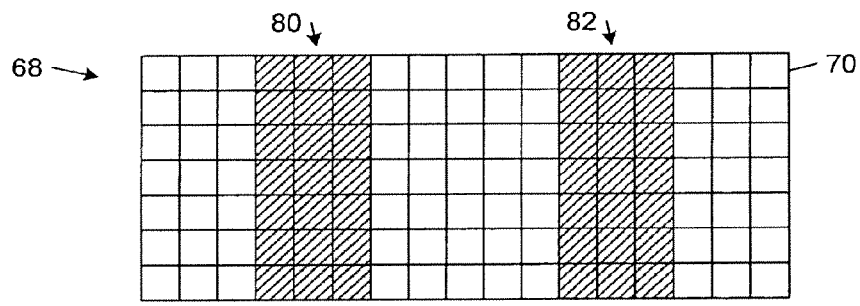
FIG. 5B is a diagrammatic view of the two-dimensional light detector array shown in FIG. 5A in which ones of the light detectors that are positioned to obtain light intensity measurements from the test region and the control region are highlighted.

As shown in FIGS. 5A and 5B, the reflected or fluorescing light from the test region 16 is received by only a subset 80 of the light detectors 70 in the array 68. Similarly, the reflected or fluorescing light from the control region 18 is received by only a subset 82 of the light detectors 70 in the array 68. Thus, the signals front the light detectors in the subsets 80, 82 provide relatively low noise light intensity measurements of the light reflected or fluorescing from the test region 16 and the control region 18, respectively.

Figure 6:
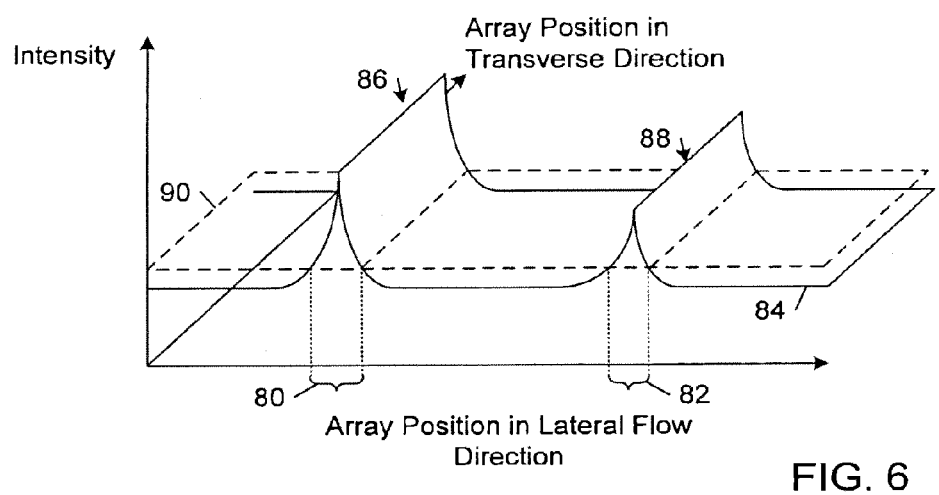
FIG. 6 is an exemplary graph of light intensity plotted as a function of position in the two-dimensional light detector array shown in FIGS. 5A and 5B.

The data analyzer 46 is operable to process the signals that are generated by the individual light detectors 70 to identify the ones of the light intensity measurements that are obtained from the regions of interest (e.g., the test region 16 and the control region 18). Referring to FIG. 6, in one illustrative example, the light detector array 68 produces a set of light intensity signals that are represented by a three-dimensional surface 84. In this example, the surface 84 includes higher intensity measurements 86, 88 obtained by the light detectors 70 in the subsets 80, 82 of the light detector array 68. With respect to this example, the data analyzer 46 may identify the light intensity measurements that are obtained from the test region 16 and the control region 18 by thresholding the surface 84 at an intensity threshold level 90. In some implementations, the threshold that is used in the thresholding process is constant across the strip or region of interest. For example, in some implementations, the threshold may be slanted or have local variations to account for variations in illumination or diffusion of the analytes. The ones of the light intensity measurements that are above the threshold level 90 are identified as having come from the test region 16 and the control region 18. Additional information, such as the relative positions of the light detector array 68 from which the identified ones of the light intensity measurements were obtained, may be used by the data analyzer 46 to correlate the identified light intensity measurements with the test region 16 and the control region 18.

Figure 7:
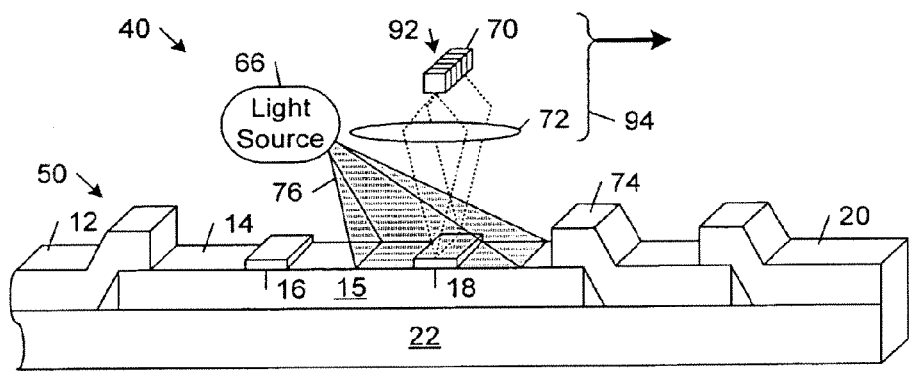
FIG. 7 is a diagrammatic view of an implementation of the diagnostic test system shown in FIG. 3 that includes a linear light detector array obtaining light intensity measurements from regions of a test strip.

B. Obtaining Separable Localized Light Intensity Measure Using a Linear Light Detector Array FIG. 7 shows an implementation of the test strip 50 that is the same as the implementation shown in FIG. 5A and an implementation of the diagnostic test system 40 that is the same as the implementation shown in FIG. 5A except that this implementation includes a linear light detector array 92 instead of the two-dimensional array 68 of light detectors 70. In this implementation, the diagnostic test system 40 additionally includes a mechanism (not shown) for imparting relative motion between the optical inspection components 94 (i.e., the light source 66, the lens 72, and the linear light detector array 92) and the test strip 50. The motion-imparting mechanism may be any one of a wide variety of different mechanisms, including a motorized carriage that moves the optical inspection components relative to the test strip 50 on a pair of rails, and one or more motorized drive wheels that move the test strip 50 relative to the optical inspection components. In the illustrated embodiment, the optical inspection components 94 are shown moving relative to the test strip 50 in the direction of arrow 96 (i.e., in the lateral flow direction). The linear light detector array 92 is oriented in a direction transverse to the direction of motion of the optical inspection components 94.

In operation, the light source 66 illuminates a region of the exposed portion of the detection zone 15 with light 76 as the optical inspection components 94 are moved relative to the test strip 50. The illuminating light may be broadband or narrowband and may be polarized or non-polarized. The linear light detector array 92 obtains separable localized light intensity measurements from a narrow portion of the illuminated region of the detection zone 15. In general, the light intensity measurements may be unfiltered or they may be filtered in terms of wavelength or polarization. The light detector array 68 may be synchronized with the light source 66. In general, the light detector array 68 may measure light intensity while the detection zone 15 is being illuminated or after the light source 66 has illuminated the detection zone 15. Light reflected or fluorescing from the detection zone 15 is focused by the lens 72 onto the individual light detectors 70 of the light detector array 92. Each of the light detectors 70 receives light from a respective localized region of the detection zone 15. That is, each light detector 70 is able to resolve or separably image a respective localized region of the detection zone 15. The light detectors 70 produce signals representative of the amount of light received from the respective localized regions. These signals may be stored in a memory or they may be transmitted to the data analyzer 46 for processing.

The data analyzer 46 is operable to process the signals that are generated by the individual light detectors 70 to identify the ones of the light intensity measurements that are obtained from the regions of interest (e.g., the test region 16 and the control region 18). In some implementations, the surface of the detection zone 15 is substantially homogeneous in the direction transverse to the lateral flow direction. In these implementations, the signals from the light detectors in the linear array 92 may be aggregated without substantial loss of information.

Figure 8:
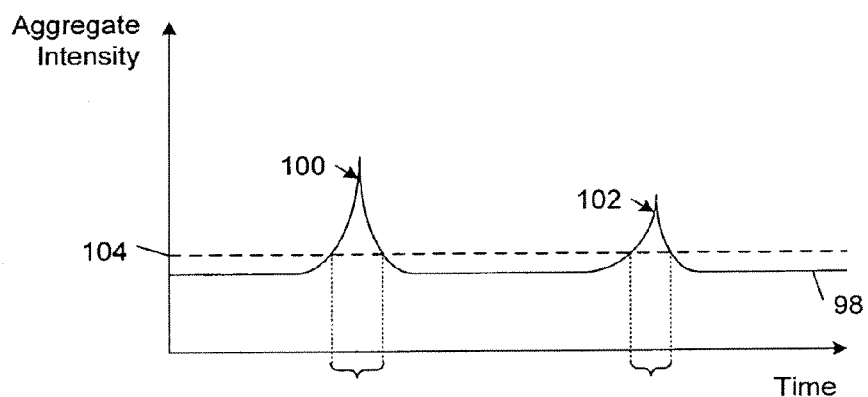
FIG. 8 is an exemplary graph of aggregate light intensity obtained by the linear light detector array shown in FIG. 7 plotted as a function of time.

FIG. 8 shows an exemplary graph 98 of the aggregated intensity measurements that are produced by the linear light detector array 92 plotted as a function of time. In this example, the graph 98 includes higher intensity aggregate intensities 100, 102 when the light detectors 70 in the array 92 are positioned over the test region 16 and the control region 18. With respect to this example, the data analyzer 46 may identify the light intensity measurements that are obtained from the test region 16 and the control region 18 by thresholding the graph 98 at an intensity threshold level 104. The ones of the light intensity measurements that are above the threshold level 104 are identified as having come from the test region 16 and the control region 18. Additional information, such as the relative times the identified ones of the light intensity measurements were obtained, may be used by the data analyzer 46 to correlate the identified light intensity measurements with the test region 16 and the control region 18.

Figure 9:
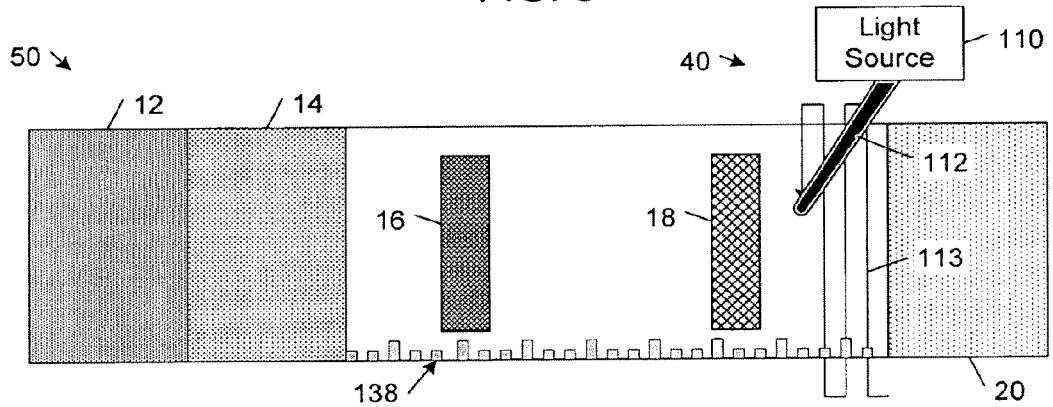
FIG. 9 is a diagrammatic top view of an implementation of the diagnostic test system shown in FIG. 3 that includes a light source scanning a light beam over regions of a test strip.

C. Obtaining Separable Localized Light Intensity Measurements Using a Scanning Light Source FIG. 9 shows an implementation of the test strip 50 that is the same as the test strip 10 shown in FIG. 1 and an implementation of the diagnostic test system 40 that includes a light source 110 that is operable to scan a light beam 112 across the exposed area of the detection zone 15. The light beam 112 may be broadband or narrowband and may be polarized or non-polarized. In general, the light source 110 may scan the light beam 112 across the exposed area of the detection zone 15 along any path that includes the test region 16 and the control region 18, including in a direction transverse to the lateral flow direction and a direction parallel to the lateral flow direction. In the illustrated embodiment, the light source 110 scans the light beam 112 along a circuitous zigzag path across the exposed area of the detection zone 15. In some implementations, the light source 110 includes a light emitter, such as a light-emitting diode or a laser, and one or more optical components (e.g., one or more lenses and a rotating mirror) for shaping and scanning the emitted light to produce the beam 112.

In the implementation shown in FIG. 9, the diagnostic test system 40 may obtain separable localized light intensity measurements using any type of single-element or multi-element light detector that has a field of view that encompasses the path of the light beam 112 across the exposed area of the detection zone 15 or that tracks the localized regions of the detection zone 15 as they are illuminated by the light beam 112. In general, the light intensity measurements may be unfiltered or they may be filtered in terms of wavelength or polarization. The light detector array may be synchronized with the light source. In general, the light detector array may measure light intensity while the detection zone 15 is being illuminated or after the light source has illuminated the detection zone 15. Because the light beam 112 illuminates only a single localized region of the detection zone 15 at a time, the light obtained by the light detector corresponds to the light reflected or fluorescing from the illuminated localized region. Therefore, each data point of the signal that is generated by the light detector correlates with a respective localized region and has a higher signal-to-noise ratio than comparable measurements obtained from larger regions of the detection zone 15.

The data analyzer 46 is operable to process the signals that are generated by the light detectors to identify the ones of the light intensity measurements that are obtained from the regions of interest (e.g., the test region 16 and the control region 18). For example, in some implementations, the data analyzer 46 may identify the light intensity measurements that are obtained from the test region 16 and the control region 18 by thresholding the time-varying light intensity measurement signal that is generated by the light detector. The ones of the light intensity measurements that are above the threshold level are identified as having come from the test region 16 and the control region 18. Additional information, such as the relative times the identified ones of the light intensity measurements were obtained, may be used by the data analyzer 46 to correlate the identified light intensity measurements with the test region 16 and the control region 18.

Figure 10:
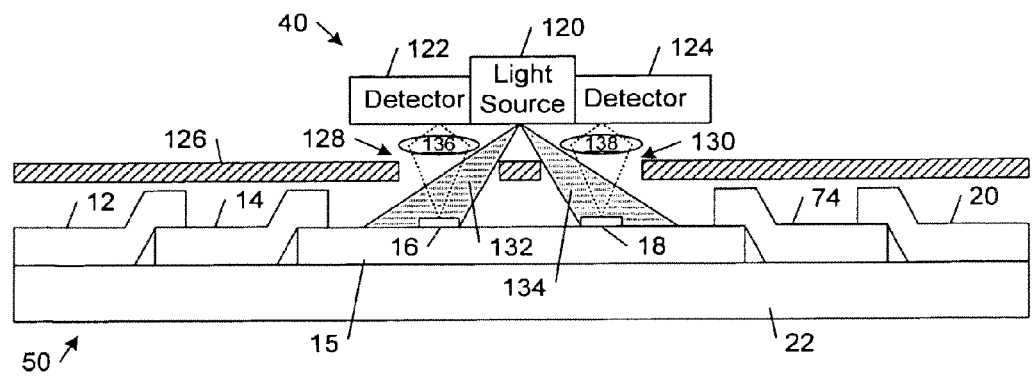
FIG. 10 is a diagrammatic side view of an implementation of the diagnostic test system shown in FIG. 3 that includes an aperture plate allowing selective detection of light from the test region and the control region of a test strip.

D. Obtaining Separable Localized Light Intensity Measurements through an Aperture FIG. 10 shows an implementation of the test strip 50 that is the same as the implementation shown in FIG. 5A and an implementation of the diagnostic test system 40 that includes a light source 120 and a pair of light detectors 122, 124. The light source 120 may be implemented by one or more light-emitting diodes that generate a relatively broad beam of light that illuminates the regions of interest in the detection zone 15. The light detectors 122, 124 may be implemented by single-element light detectors or multi-element light detectors.

An aperture plate 126 defines a pair of apertures 128, 130 through which light intensity measurements are obtained by the light detectors 122, 124. In the illustrated implementation, the apertures 128, 130 are positioned over the test region 16 and the control region 18 when the test strip 50 is loaded in the port 48 of the diagnostic test system 40. In general, the apertures 128, 130 are designed to selectively allow light reflected or fluorescing from the regions of interest in the detection zone to reach the detectors 122, 124. In the illustrated embodiment, the apertures 128, 130 also allow the regions of interest in the detection zone 15 to be illuminated by the light source 120. The apertures 128, 130 typically are positioned as close as practical to the regions of interest. In some implementations, the apertures 128, 130 substantially match the test region 16 and the control region 18 in size, shape, and orientation.

In operation, the light source 120 illuminates the test region 16 and the control region 18 with light 132, 134 that is transmitted through the apertures 128, 130. The illuminating light may be broadband or narrowband and may be polarized or non-polarized. The light detectors 122, 124 obtain separable localized light intensity measurements from the illuminated regions of the detection zone 15. In general, the light intensity measurements may be unfiltered or they may be filtered in terms of wavelength or polarization. The detectors 122, 124 may be synchronized with the light source 120. In general, the light detectors 122, 124 may measure light intensity while the detection zone 15 is being illuminated or after the light source 120 has illuminated the detection zone 15. Light reflected or fluorescing from the test region 16 and the control region 18 is focused by the lenses 136, 138 onto the light detectors 122, 124, respectively. In this way, the light detectors 122, 124 are able to resolve or separably image the test region 16 and the control region 18. The light detectors 122, 124 produce signals representative of the amount of light received from the test region 16 and the control region 18. If the light detectors 122, 124 are implemented by single-element detectors, the signals represent total or aggregate amounts of light received from the test region 16 or the control region 18. If the light detectors 122, 124 are implemented by multi-element detectors, the signals represent the amounts of light received from localized areas of the test region 16 and the control region 18. The signals that are generated by the light detectors 122, 124 may be stored in a memory or they may be transmitted to the data analyzer 46 for processing.

The light reflected or fluorescing from the test region 16 and the control region 18 is preferentially transmitted through the apertures 128, 130, whereas light from other regions of the test strip 50 are substantially blocked by the aperture plate 126. As a result, the signals that are generated by the light detectors 122, 124 have higher signal-to-noise ratios than comparable measurements obtained from larger regions of the detection zone 15. In addition, the light obtained by the light detectors 122, 124 substantially corresponds to the light reflected or fluorescing from the test region 16 and the control region 18, respectively. Therefore, the signals that are generated by the light detectors 122, 124 correlate with the test region 16 and the control region 18, respectively, and the data analyzer 46 can identify the ones of the light intensity measurements that are obtained from the test region 16 and the control region 18 directly. That is, the light intensity measurements generated by the light detector 122 are obtained from the test region 16 and the light intensity measurements generated by the light detector 124 are obtained from the control region 18.

E. Obtaining Separable Localized Light Intensity Measurements Using Position Markers In some implementations, the data analyzer 46 is operable to identify ones of the light intensity measurements obtained from regions of interest in the detection zone 15 based on intensity measurements obtained from at least one position marker on the test strip. The implementation of the test strip 50 shown in FIG. 9 includes an exemplary set of position markers 138. In the illustrated implementation, the position markers 138 are spaced regularly along the edge of the test strip 50. The position markers 138 include features that have a different reflectivity characteristic than the surface of the test strip 50. As a result, the measurements obtained near the edge of the test strip 50 vary in intensity in accordance with the patter of the position markers 138. In this way, the position markers encode the position along the test strip 50 in the lateral flow direction.

In these implementations, the data analyzer 46 correlates the light intensity measurements with the position along the test strip 50 in the lateral flow direction. Based on this information and predetermined information correlating the locations of the regions of interest with the pattern of position markers 138, the data analyzer 46 can identify the ones of the light intensity measurements corresponding to the regions of interest.

III. Diagnostic Testing Based on Sets of Measurements from Localized Regions

The embodiments that are described in detail below increase the accuracy of the lateral flow assay results by obtaining respective sets of measurements from localized regions of the test strip from which additional analytical information about these regions may be obtained. This additional information is used to separate target measurements from background noise and to derive more accurate estimates of target parameter values.

Figure 11:
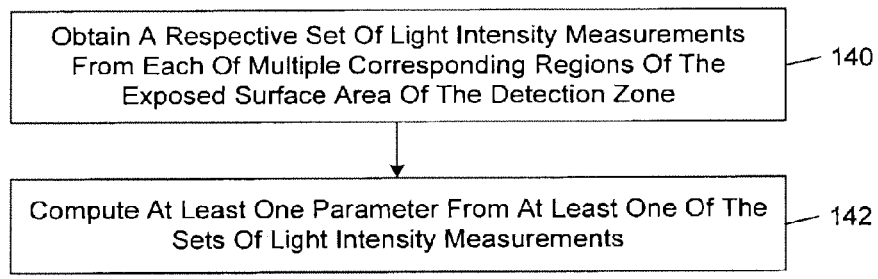
FIG. 11 is a flow diagram of an embodiment of a method of a diagnostic test method.

FIG. 11 shows an embodiment of a diagnostic test method that is executable by the implementations of the diagnostic test system 40 described above. In accordance with this method, the reader 44 obtains a respective set of light intensity measurements from each of multiple corresponding regions of the exposed area of the detection zone (block 140). The illuminating light may be broadband or narrowband and may be polarized or non-polarized. The reader 44 may obtain the sets of light intensity measurements from each of the corresponding regions using a single-element detector or a multi-element light detector. In general, the light intensity measurements may be unfiltered or they may be filtered in terms of wavelength or polarization. The light detector may be synchronized with the light source. In general, the light detector may measure light intensity while the detection zone 15 is being illuminated or after the light source has illuminated the detection zone 15.

In this embodiment, each of the localized regions from which the light intensity measurements are obtained by the reader 44 may or may not be characterized by at least one surface dimension that is smaller than the dimension of the exposed area of the detection zone that is transverse to the lateral flow direction. In some implementations, however, each of these localized regions has a surface dimension that is approximately the same size or smaller than the narrowest dimension of a region of interest in the detection zone (e.g., the test region, the control region, or a region of an immobilized labeled or unlabeled complex).

After the reader 44 has obtained the sets of light intensity measurements (block 140), the data analyzer 46 computes at least one parameter from at least one of the sets of light intensity measurements (block 142). In this process, the data analyzer 46 may use the sets of light intensity measurements to derive more accurate estimates of target parameter values. Alternatively, the data analyzer 46 may use the sets of light intensity measurements to isolate the measurements corresponding to regions of interest (e.g., the test region 16 and the control region 18) from the measurements corresponding to other regions of the test strip 50. These isolated measurements have higher signal-to-noise ratios than aggregate measurements that include measurements from regions outside of the regions of interest.

Figures 12A, 12B:
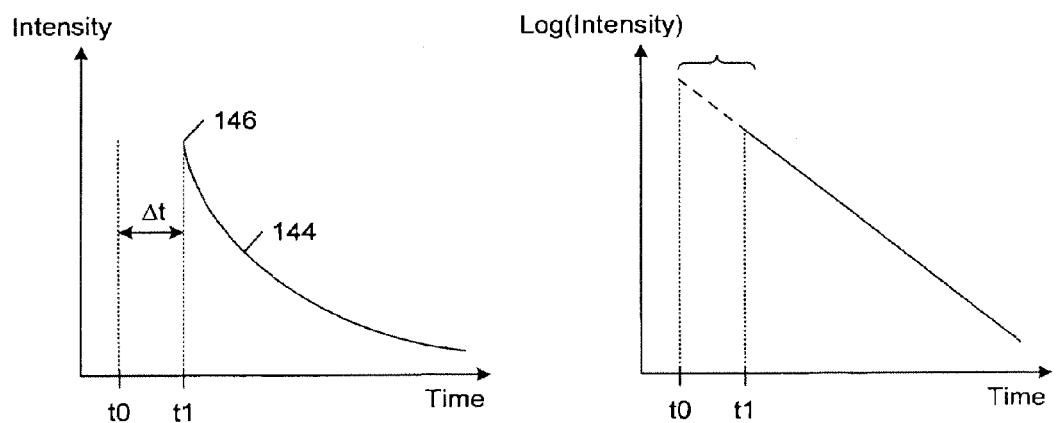
FIG. 12A is a graph of intensity plotted as a function of time.
FIG. 12B is a graph of the logarithm of the intensity values shown in FIG. 12A plotted as a function of time.

Referring to FIGS. 12A and 12B, in one embodiment, the reader 44 obtains sets of light intensity measurements that represent changes in the fluorescence response of the regions of interest in the detection zone 15 over time. In one approach designed for test strips with fluorescent labels, the light source is pulsed and the light detector obtains a series of light intensity measurements from the corresponding regions after each light pulse. FIG. 12A shows one exemplary graph 144 representing a series of light intensity measurements that are obtained by the reader 44. In this example, the light source is pulsed at a time t0 and the light intensity measurements are obtained beginning at a time t1, which follows the time t0 by a delay period Δt. Because of the delay period Δt, the peak intensity measurement 146 does not represent the true peak intensity of the fluorescence emitted from the region of interest. The data analyzer 46 derives a more accurate estimate of the peak fluorescence by computing a decay parameter τ from the graph in accordance with an exponential decay model (Intensity $\propto e^{-t/\tau}$) and extrapolating the intensity value back to the time t0 to obtain an estimate of the peak intensity, as shown in FIG. 12B. Because this estimate of the peak intensity value is closer to the onset of the actual fluorescence from the region of interest, this estimate provides a more accurate measure of the peak fluorescence value than the actual measured peak intensity 146.

In some implementations, the data analyzer 46 computes a parameter value from respective ones of the peak intensity parameter values corresponding to multiple regions of interest in the detection zone 15. For example, in some implementations, the data analyzer 46 may compute the ratio of peak intensity values estimated for first and second test regions in order to obtain a measure of the relative concentration of two target analytes in a sample.

Figure 13A:
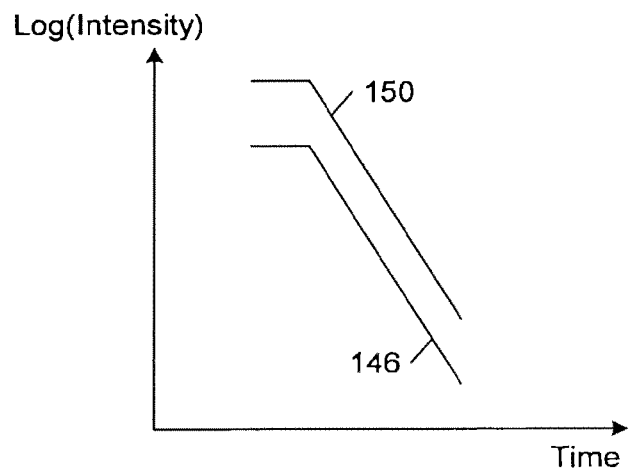
FIGS. 13A and 13B show respective graphs of the logarithms of two sets of light intensity measurements plotted as functions of time.
Figure 13B:
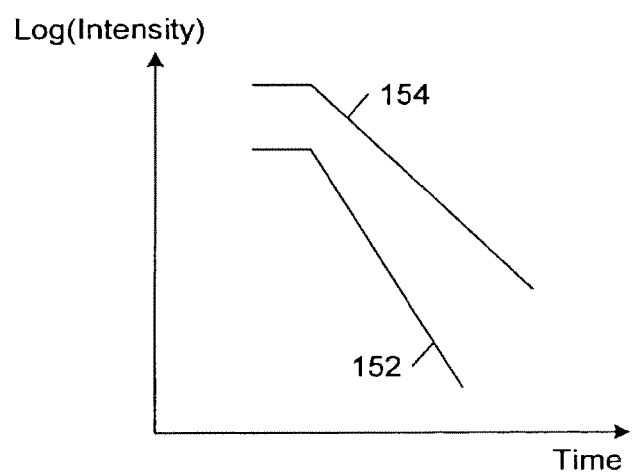

The temporal responses of the localized regions from which the intensity measurements are obtained also may be used to associate these measurements with different fluorescent sources. For example, FIG. 13A shows two log intensity plots 148, 150 that are derived two sets of light intensity measurements. Because these plots 148, 150 exhibit the same decay parameters (i.e., they have the same slope), the data analyzer 46 can infer that the fluorescent sources from which these sets of measurements are obtained are the same fluorescent species. FIG. 13B also shows two log intensity plots 152, 154 that are derived two sets of light intensity measurements. Because these plots 152, 154 exhibit different decay parameters (i.e., they have different slopes), the data analyzer 46 can infer that the fluorescent sources from which these sets of measurements are obtained are different fluorescent species.

In other embodiments, the wavelength responses of the localized regions from which the intensity measurements are obtained are used to associate these measurements with different fluorescent sources. For example, in some embodiments, each of the light intensity measurements that is obtained for a given one of the localized regions corresponds to a different wavelength profile (or color channel) that encompasses one or more wavelengths. In some implementations, the detection zone 15 may be illuminated with a broadband light source and the light detector may be configured to obtain multiple measurements from each of the corresponding regions corresponding to different target wavelength ranges of interest. In other embodiments, the reader 44 illuminates each of the corresponding regions of the detection zone 15 with light having different wavelength profiles each of which encompasses one or more wavelengths. In this regard, the reader 44 may include multiple light sources capable of generating light with different wavelength profiles or a single wavelength-tunable light source. The target wavelength ranges typically are selected to elicit different responses from various regions of interest in the detection zone. For example, in some implementations, the target wavelength ranges are selected to induce fluorescence in different respective fluorescent labels.

Figure 14:
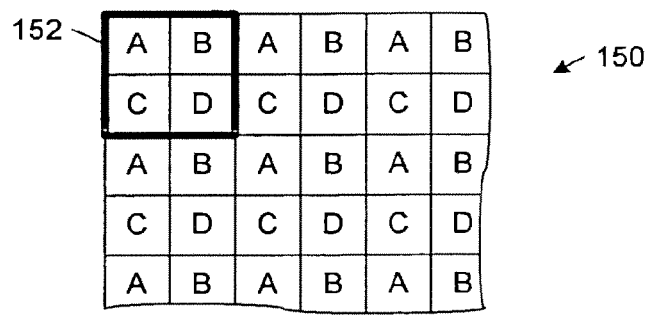
FIG. 14 is a diagrammatic view of a portion of an embodiment of a color filter array.

In some of these implementations, the reader 44 includes one or more light detectors that are configured to discriminate the different target wavelength responses of the regions of interest in the detection zone 15. FIG. 14 shows a portion of an exemplary embodiment of a color filter array 150 that includes identical sets 152 of four color filters (A, B, C, and D), each of which intercepts light that is directed toward a respective light detector of a two-dimensional light detector array (not shown). The color filters define the color channels for the light intensity measurements obtained by the light detectors. The light detectors corresponding to a give set 152 of color filters image substantially the same localized region of the detection zone 15. Therefore, the light signals that are generated by the light detectors corresponding to a given set 152 substantially correspond to the wavelength response of the imaged region in terms of the color channels A, B, C, and D.

Figure 15:
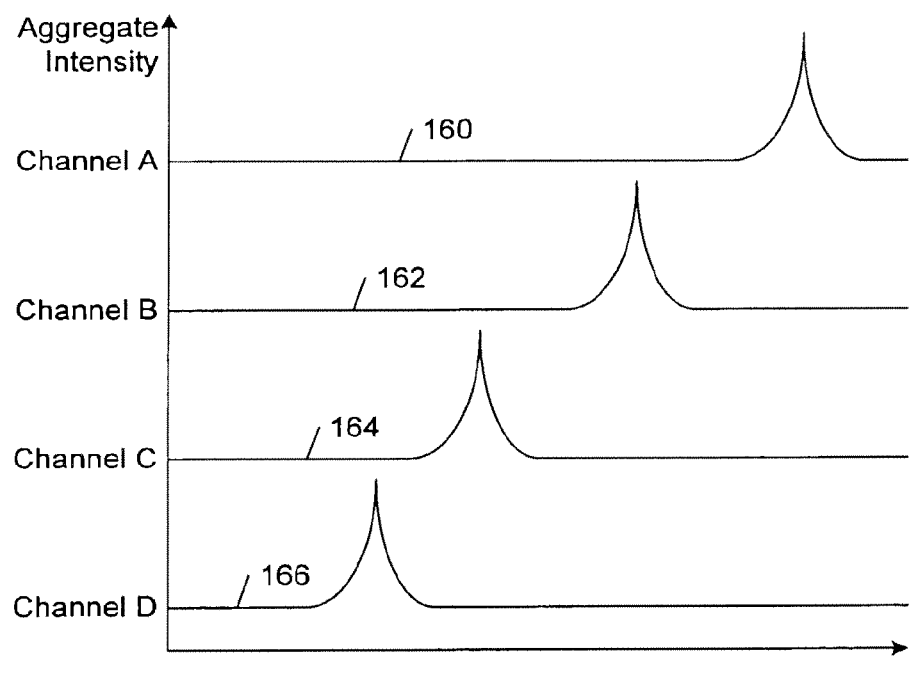
FIG. 15 is a graph of aggregate intensity for four different color channels plotted as a function of position along the lateral flow direction in a two-dimensional light detector array.

From these measurements the data analyzer 46 determines wavelength response profile across the illuminated regions of the detection zone 15. FIG. 15 shows exemplary graphs 160, 162, 164, 166 of the aggregate intensity profiles obtained from an implementation of the reader 44 that obtained light intensity measurements with a two-dimensional light detector array and the color filter array shown in FIG. 14. Each of graphs 160-166 corresponds to a respective one of the color channels A, B, C, and D that is defined by the color filter array 150. The aggregate intensity values are plotted as functions of the position in the two-dimensional light detector array along the lateral flow direction. In the illustrated example, the graphs 160-166 include peak intensity values at different respective locations in the two-dimensional light detector array. Since the array positions correlate with the locations in the detection zone 15 along the lateral flow direction, the data analyzer 46 may infer that different label species are present at these different locations in the detection zone 15. This information may be used by the data analyzer 46 to isolate the light intensity measurements corresponding to different labels from one another.

In other embodiments, the reader 44 illuminates each of the corresponding regions of the detection zone 15 with light of a different respective polarization. In these implementations, the reader 44 includes one or more light detectors that are configured to discriminate the different polarization responses of the regions of interest in the detection zone 15. From these measurements the data analyzer 46 determines polarization response profile across the illuminated regions of the detection zone 15. This information may be used by the data analyzer 46 to isolate the light intensity measurements corresponding to different labels from one another (e.g., by thresholding or detecting peak intensities).

IV. Conclusion

Some of the embodiments that are described above reduce levels of noise (e.g., noise caused by reflection of light or intrinsic fluorescence from materials in the test strip) in lateral flow assay measurements by restricting the measurements to the regions of interest on the test strip from which the desired quantitative information may be derived. In this way, these embodiments increase the signal-to-noise levels of these measurements and, thereby, improve measurement sensitivity and reduce the incidence of erroneous results. Some of these embodiments also increase the accuracy of the lateral flow assay results by obtaining respective sets of measurements from localized regions of the test strip from which additional analytical information about these regions may be obtained. This additional information may be used to isolate target measurements from background noise and to derive more accurate estimates of target parameter values. Some embodiments also are capable of accurately reading multiple analytes from the same test strip and differentiating between spatially separated labels and spectrally separated labels.

Other embodiments are within the scope of the claims.

Figure 16:
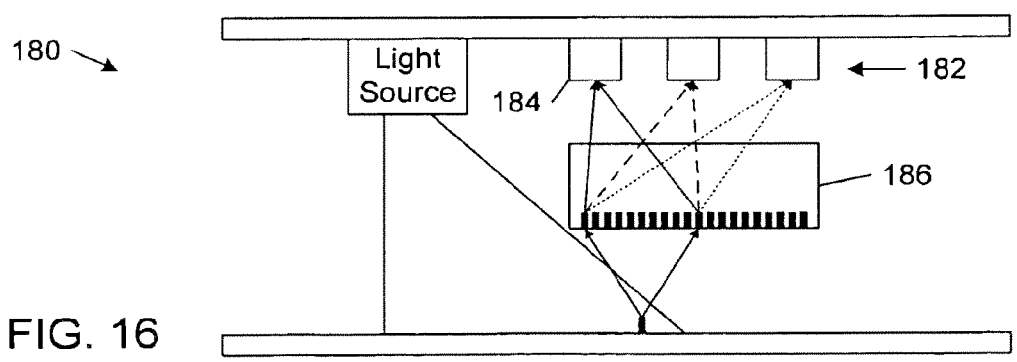
FIG. 16 is a diagrammatic side view of an implementation of the diagnostic test system shown in FIG. 3.

For example, any of the foregoing embodiments may be supplemented by diffractive optics or gratings that separate and steer different wavelengths of light to respective ones of multiple light detectors. For example, FIG. 16 shows a diagnostic test system 180 that obtains separable localized light intensity measurements using a two-dimensional light detector array 182. In this implementation, each individual detector element 184 in any individual transverse row of the detector array 182 can be the target of a specific wavelength of light that is separated and steered by a diffractive lens 186.

What is claimed is:

1. A diagnostic test system, comprising:
   a test strip comprising one or more test regions and one or more control regions, the one or more test regions comprising multiple localized regions containing an immobilized substance configured to bind a target analyte;
   a reader programed to obtain light intensity measurements from the multiple localized regions of the one or more test regions, the reader comprising
      one or more light sources configured to illuminate the multiple localized regions of the one or more test regions, and
      a light detector array that comprises individual light detectors, each individual light detector configured to obtain a separable light intensity measurement from one of the multiple localized regions of the one or more test regions; and
   a data analyzer comprising software that identifies the separable light intensity measurements obtained from the one or more test regions and computes at least one parameter from the identified separable light intensity measurements.

2. The diagnostic test system of claim 1, wherein the at least one parameter comprises a peak intensity value or an aggregative intensity value.

3. The diagnostic test system of claim 1, wherein the test strip supports lateral flow of a fluid along a lateral flow direction, and wherein at least one test region includes an area that is exposed for optical inspection and is characterized by a first dimension transverse to the lateral flow direction and a second dimension parallel to the lateral flow direction.

4. The system of claim 3, wherein each of the localized regions of the one or more test regions is characterized by at least one dimension that is the same size or smaller than the second dimension of the at least one test region.

5. The system of claim 1, further comprising a mechanism for imparting relative motion between the test strip and the reader.

6. The system of claim 5, wherein the mechanism comprises a motorized carriage that moves the test strip relative to the reader.

7. The system of claim 5, wherein the test strip supports lateral flow of a fluid along a lateral flow direction and wherein the mechanism is configured to move the reader relative to the test strip in the lateral flow direction.

8. The system of claim 7, wherein the light detector array comprises a linear light detector array oriented in a direction transverse to the direction of motion of the reader.

9. The system of claim 1, wherein the data analyzer is configured to identify the separable light intensity measurements obtained from the test region based at least in part on intensity measurements obtained from at least one position marker on the test strip.

10. A diagnostic test system, comprising:
    a reader programed to measure an intensity of a light signal arising from a measurement zone of a lateral flow assay test strip as a result of the presence of a labeled target analyte complex immobilized in the measurement zone, the reader further configured to measure an intensity of a light signal arising from a control zone of the lateral flow assay test strip as a result of the presence of a labeling substance immobilized in the control zone, the lateral flow assay test strip comprising multiple localized regions, the reader comprising
       a light source configured to illuminate the lateral flow assay test strip, and
       a plurality of light detectors, each light detector configured to detect intensity of light signals arising from one of the multiple localized regions and generate a light intensity measurement; and
    a data analyzer programed to individually analyze each light intensity measurement and isolate light intensity measurements arising from the measurement zone and the control zone from light intensity measurements that do not arise from the measurement zone or the control zone, the data analyzer further configured to compute at least one parameter from the isolated light intensity measurements arising from the measurement zone and the control zone.

11. The system of claim 10, wherein the measurement zone comprises immobilized compounds configured to bind the labeled target analyte complexes and retain the labeled target analyte complexes in the measurement zone.

12. The system of claim 10, wherein the control zone comprises a compound configured to bind the labeling substance and retain the labeling substance in the control zone.

13. The system of claim 10, wherein the data analyzer is further configured to determine the presence of a labeled target analyte complex immobilized in the measurement zone based on isolated light intensity measurements arising from the measurement zone.

14. The system of claim 10, wherein the data analyzer is further configured to determine when sufficient quantity of the labeling substance has accumulated in the control zone based on isolated light intensity measurements arising from the control zone.

15. The system of claim 10, further comprising a test result indicator configured to indicate the presence of a labeled target analyte complex immobilized in the measurement zone.

16. The system of claim 15, wherein the test result indicator comprises one or more lights or an alphanumeric display.

17. The system of claim 15, wherein the test result indicator is further configured to indicate completion of an assay test when sufficient quantity of the labeling substance has accumulated in the control region.

18. The system of claim 10, wherein the reader is configured to communicate light intensity measurements to the data analyzer over a wireless connection.

\* \* \* \* \*